(12) United States Patent
Greenbank et al.

(10) Patent No.: US 6,422,059 B1
(45) Date of Patent: Jul. 23, 2002

(54) APPARATUS FOR DETECTING CHANGES IN CONCENTRATIONS OF COMPONENTS OF FLUID MIXTURES

(75) Inventors: Micahel Greenbank, Monaca; David T. Doughty, Moon Township; Mark Allen Bollinger, Pittsburgh, all of PA (US)

(73) Assignee: Calgon Carbon Corporation, Pittsburgh, PA (US)

( * ) Notice: Subject to any disclaimer, the term of this patent is extended or adjusted under 35 U.S.C. 154(b) by 0 days.

(21) Appl. No.: 09/630,112

(22) Filed: Aug. 1, 2000

(51) Int. Cl.[7] ................ G01N 19/10; G01N 30/02; C25B 11/12
(52) U.S. Cl. .................. 73/23.2; 204/294; 422/70
(58) Field of Search ............... 73/23.2, 23.28, 73/23.4; 204/294, 403; 205/560, 743; 422/70, 98

(56) References Cited

U.S. PATENT DOCUMENTS 4,118,194 A * 10/1978 Raleigh et al. ............ 422/98
4,343,767 A * 8/1982 Long et al. ............... 422/70

* cited by examiner

Primary Examiner—Hezron Williams
Assistant Examiner—Jay L. Politzer
(74) Attorney, Agent, or Firm—Cohen & Grigsby, P.C.

(57) ABSTRACT

An apparatus is provided for the detection of changes in concentrations or amounts of components of a fluid mixture by measuring changes in an electrical or a mechanical property of a sensing element when the sensing element is exposed to the fluid mixture. The preferred property of the sensing element to be measured is its electrical resistance which changes when the sensing element adsorbs at least one component of the fluid mixture.

11 Claims, 8 Drawing Sheets

APPARATUS FOR DETECTING CHANGES IN CONCENTRATIONS OF COMPONENTS OF FLUID MIXTURES

FIELD OF THE INVENTION

The present invention relates to an apparatus for detecting changes in concentrations of components of a fluid mixture by relating changes in an electrical or mechanical property of a sensing means to such changes in concentrations. In particular, this invention relates to such an apparatus based on a change in a resistance of a sensing means made of an activated carbon material as the concentrations change.

BACKGROUND OF THE INVENTION

Due to the capability of activated carbon to remove a wide variety of chemical compounds from fluid mixtures, it has been widely used to purify such mixtures. The removal is effected by physical adsorption of these contaminants in the micropores of the activated carbon which are developed during the manufacturing process. The activated carbon is said to be spent when its micropores are filled with the contaminants and it no longer has any capacity for further adsorption. When the activated carbon bed is spent, the concentration of a contaminant in the treated fluid stream increases rapidly. This event is referred to as the breakthrough of the go contaminant. To ensure a properly treated stream, the activated carbon bed must be replaced at some time prior to the first breakthrough of the contaminants. Since the concentrations and the types of contaminants may vary during the time during which the carbon bed is on stream, the breakthrough point cannot be precisely predicted and, therefore, the quality of the treated fluid stream must be monitored by frequent periodic testing, which sometimes can be costly. Therefore, there is a need for a device that can warn the user when the carbon bed is nearly spent without the requirement for periodic testing of the treated fluid. Such a device preferably stays on stream continuously and detects an increase in the contaminant level near the outlet of the carbon bed to provide an efficient use thereof. Such a device is also useful in purification systems employing media other than activated carbon.

Many sensors have been proposed in the art, but they have been directed to detecting only hydrocarbon contaminants and, thus, limited in their applications. U.S. Pat. Nos. 5,079,944 and 5,150,603 disclosed hydrocarbon vapor sensors and systems for detecting leaks from underground storage tanks. The heart of the sensors of these patents was a sensing element made of a conductive polymer, the resistance of which changed when hydrocarbons absorbed into and swelled the polymer matrix. In one embodiment, the conductive polymer comprised a polymeric tape carrying conductive carbon particles. In another embodiment, the conductive polymer was an elastomer or a silicone rubber filled with silver-coated glass spheres or metallic silver flakes. The presence of hydrocarbon vapor was ascertained when the resistance of the sensing element increased rapidly. However, this sensor would not be able to detect any contaminant that does not absorb readily into and swell the polymer matrix.

Moyer et al. disclosed the use of an end-of-service-life indicator for organic vapor cartridge respirators (E. S. Moyer et al., "A Preliminary Evaluation of an Active End-of-Service-Life Indicator for Organic Vapor Cartridge Respirators," Am. Ind. Hyg. Asssoc. J., Vol. 54, No. 8, pp. 417–425 (1993)). The sensor of this study comprised a mixture of silicone rubber and carbon particles deposited on a substrate. The detection of organic vapor also relied on the swelling of the silicone matrix, resulting in an increase in the resistance of the silicone/carbon conducting film. Thus, a contaminant that does not swell the silicone would not be detected because the resistance of the film would not change.

Marchand reported the construction of an organic vapor sensor which comprised a small bed of activated carbon cloth (E. G. Marchand, Ph.D. Thesis, Michigan Technological University, 1996). Experiments under flow conditions were done only with trichloroethylene in dry air. The electrical resistance of the carbon cloth began to increase sharply when the challenge gas is admitted into the carbon cloth sensor long before the breakthrough occurred. There was no suggestion as to how a sensor may be configured to indicate reliably a breakthrough by directly relating a change in this electrical property to the breakthrough point.

Therefore, it is an object of the present invention to provide an apparatus for detecting changes in concentrations of a range of minor components of a fluid mixture. It is a further object of the present invention to provide a detection apparatus that relates the change in electrical resistance, or mechanical properties, of a carbon-based sensing element to the change in concentrations of the minor components. It is still another object of the present invention to provide an apparatus for detecting the breakthrough of minor components of a fluid mixture from an activated carbon bed used for the purification thereof.

SUMMARY OF THE INVENTION

The present invention provides an apparatus for detecting changes in concentrations, or amounts of minor components, of a fluid mixture that measures the changes in electrical resistance or mechanical properties of a sensing element when the sensing element is exposed to the fluid mixture. Minor components of a fluid mixture, as are referred to herein, are those having weight-based or molar concentrations less than about 50 percent. Such an apparatus will hereinafter also be referred to as a detector. The present invention measures changes in other electrical or mechanical properties of the sensing element, such as electrical capacitance, mechanical strength or dimensional change, when such changes occur in relation to changes in concentrations or amounts of the minor components of the fluid mixture. When the measured electrical or mechanical property of the sensing element changes, the detector indicates a change in a concentration. The means for detecting the measurable property varies depending upon the property and includes, for example, electrical detectors, Wheatstone bridge related technologies or stress or strain gauges. The present invention further includes, in another embodiment, a sensing element for use in detecting changes in concentrations minor components of a fluid mixture, said element comprising an activated carbon cloth having a connecting means for measuring said changes.

In general, the detector of the present invention comprises at least first and second sensing elements that are carbon-based, or are of other suitable materials, such as metal, and have substantially the same composition, electrical resistance and dimensions. The electrical resistances of the two sensing elements preferably differ by less than 10 percent; more preferably, less than 5 percent. One particularly suitable carbon for the manufacture of the sensing elements is activated carbon fiber or activated carbon cloth ("ACC") which is manufactured in thermal processes from raw materials made of woven or non-woven natural, man-made, or synthetic fibers and which possesses a high surface area for adsorption of a wide variety of compounds. ACC typically has a low electrical resistance, and this resistance changes substantially when the ACC adsorbs even a small amount of contaminants. This property is used advantageously in the detector of the present invention to detect contaminants in fluid streams.

Alternatively, the sensing elements may be made of an electrically conducting sheet comprising a conductively effective amount of activated carbon particles immobilized in a polymeric fiber mixture. The present invention may be used in conjunction with a system, such as a purification system. When used with a purification system, the first sensing element is exposed to the fluid mixture, the change in the concentration of one or more minor components is detected. Preferably, the first sensing element is positioned at a location where the fluid mixture initially has a first substantially stable composition. The second sensing element serves as a reference and remains exposed to the same fluid mixture having the first substantially stable composition. In many situations in which the fluid mixture is being purified by the removal of the minor components, the fluid mixture having the first substantially stable composition is that substantially devoid of the minor components. As the concentration of a minor component in this mixture increases, the changes in such concentration are detected. Initially, the electrical resistances or mechanical properties of the first and second sensing elements are substantially equal when exposed to the same fluid mixture having the first substantially stable composition. When the concentration of a minor component of the fluid mixture begins to change, measurable electrical or mechanical properties of the first sensing element also begin to change in comparison to that of the second sensing element when exposed to the fluid mixture near the outlet of the purification system. The present invention will detect that a minor component of the fluid mixture is about to breakthrough and a warning signal may be given.

In a preferred embodiment of the present invention, the detector comprises two sensing elements made of ACC which are spaced apart in an elongated enclosure having an inlet and an outlet. An adsorbent capable of removing the minor components of the fluid mixture is disposed in the elongated enclosure between the sensing elements. Examples of such an adsorbent are activated carbon that have the form, for example, of granules, pellets, or spheres; natural or synthetic zeolite; silica gel; activated alumina; and any of these adsorbents modified to enhance their adsorption capacities. Electrically conducting leads are provided to measure the electrical resistance of each of the carbon-cloth sensing elements. The fluid mixture, having a first substantially stable composition, enters the detector and contacts, in sequence, the first sensing element, the adsorbent portion, and the second sensing element. This fluid stream is preferably a split stream of the fluid mixture flowing through the enclosure and is taken from a point near the outlet of the purification system. Initially, the compositions of the fluid contacting the first and second sensing elements are substantially the same and both sensing elements exhibit substantially the same electrical or mechanical properties. The properties are used to establish a base line.

When used with a purification system and the capacity of the purification system has been exhausted, the concentrations of the minor components of the fluid mixture begin to increase. The adsorption of the minor components in the ACC material of the first sensing element results in a change in the electrical resistance thereof. The change is positive or negative depending on the types of the minor components and the fluid mixture. Due to the adsorption of the minor components in the adsorbent portion between the first and second sensing elements, the resistance of the second sensing element remains at the base line value for a short time thereafter. Thus, a differential in the resistances indicates that a breakthrough of the minor components from the purification system is about to occur. A means for detecting the differential is provided and can be designed to notify an operator of the system so that appropriate actions may be taken to ensure a continued quality of the treated fluid stream. Several similar detectors of the present invention may be used in conjunction with a purification system to indicate the degree of exhaustion of the capacity of the purification system. When used in this manner, the detectors are arranged at intervals along the system.

In another embodiment of the present invention, each carbon-based sensing element is housed in a separate enclosure. The first sensing element is exposed to a stream of the fluid mixture, the change in the composition of which is desired to be detected. This first sensing element is located before the outlet of the purification system to detect the minor components before they breakthrough. The second sensing element serving as the reference is always exposed to a split stream of the treated fluid. At the beginning of the purification operation, the compositions of the fluid streams flowing through the sensing elements are substantially the same. Thus, the differential in the resistances of the sensing elements is near zero. As the first minor component of the fluid mixture reaches the location of the first sensing element, its resistance begins to change rapidly while that of the reference sensing element remains substantially constant. This change signals that the first minor component is about to breakthrough from the fluid treatment system.

DETAILED DESCRIPTION OF THE PREFERRED EMBODIMENTS

Figure 1:
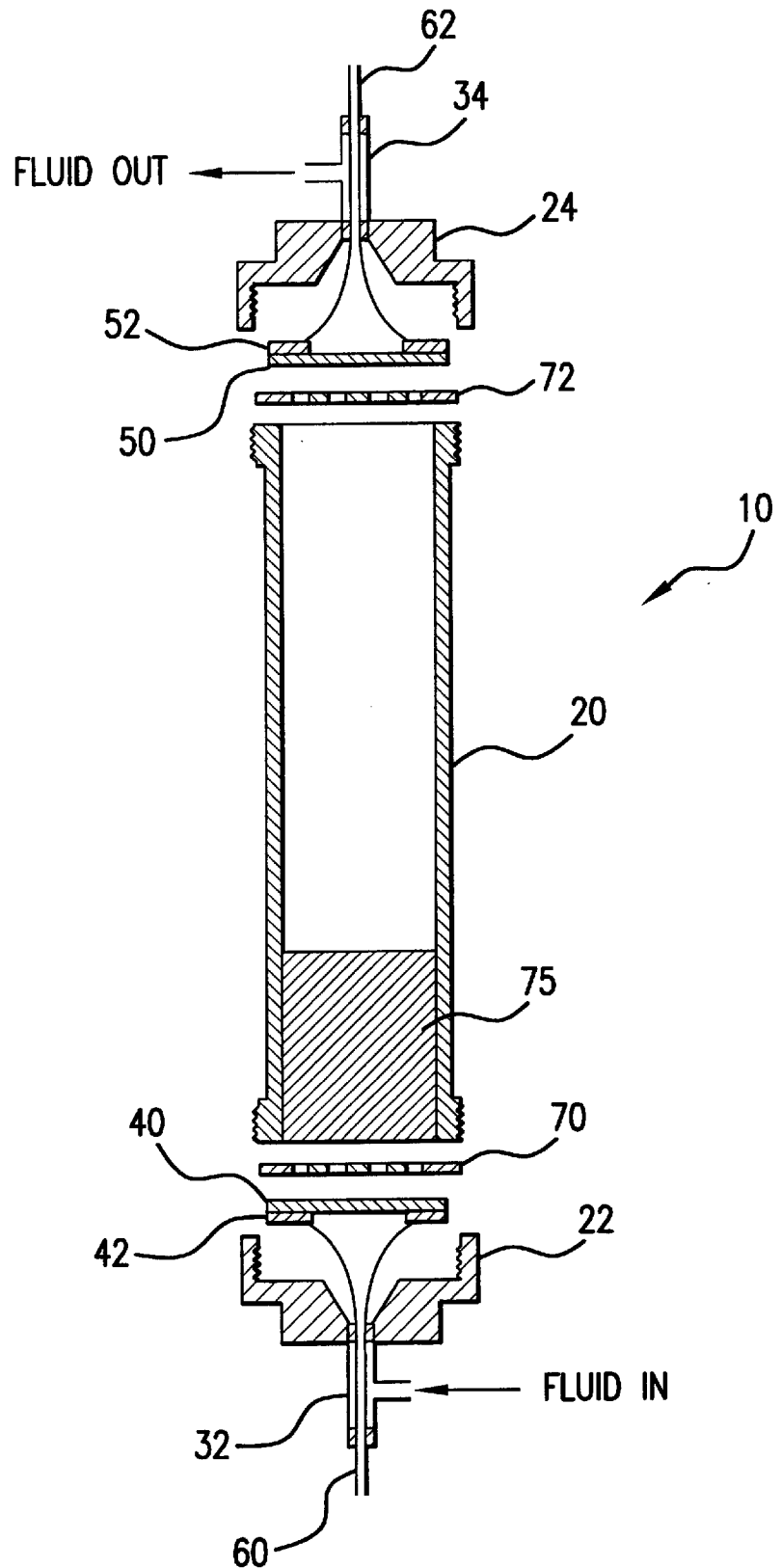
FIG. 1 is a schematic diagram of a preferred embodiment of the detector of the present invention.

A preferred embodiment of the present invention is substantially as shown in the schematic diagram of FIG. 1. Detector 10 comprises a housing section 20 having two open ends, a length of about 3 feet, and a diameter of about 3 inches. Section 20 is preferably a plastic pipe or, when the fluid mixture is under a superatmospheric pressure, section 20 may be advantageously made of a metal. The length and diameter of section 20 may be varied depending on the application. For example, a length of less than 1 foot is generally adequate for most applications. The diameter of section 20, as will be seen, will determine the accuracy of the measurement of the resistance of the sensing elements. A larger diameter is generally preferred. Section 20 is sealed with end caps 22 and 24. End caps 22 and 24 include pipe fittings 32 and 34 for conducting a stream of fluid into and out of section 20.

Sensing elements 40 and 50 are positioned in end caps 22 and 24. When the end caps 22 and 24 and the section 20 are made of a metal, each sensing element 40 or 50 is disposed between two non-conducting gaskets (not shown) to electrically isolate it from the detector housing. Each sensing element is made of one or more layers of ACC preferably having a dimension such that it completely covers the cross sectional area of the pipe section. Both sensing elements are preferably made of substantially the same ACC material so that their electrical resistances are substantially equal. Each sensing element is provided with a zinc electrode 42 and 52 attached to the ACC material for a connection with electrical leads 60 and 62, respectively. Plastic screens 70 and 72 provide mechanical support to the sensing elements 40 and 50.

In a preferred embodiment, an amount of an adsorbent 75 having a large pore volume for adsorption of the first minor component of the fluid mixture is contained in the pipe section 20 to provide a substantial time between the moments when the first and second sensing elements begin to contact the first minor component. This adsorbent may be activated carbon, zeolite, activated alumina, silica gel, or mixtures thereof.

Electrical leads 60 and 62 are preferably connected to a Wheatstone bridge for the detection of changes in the electrical resistance of the sensing elements. Initially, a stream of the fluid mixture devoid of minor components is conducted through the present invention and the Wheatstone bridge is balanced. When the concentration of the first minor component of the fluid mixture flowing through the detector begins to increase, the carbon cloth of the first sensing element begins to adsorb this component, resulting in a change in its resistance and an off-set voltage in the Wheatstone bridge. This voltage may be used to warn the user of the fluid purification system that the first minor component of the fluid mixture has broken through at the point of the detection.

EXAMPLE 1

Detection of Carbon Tetrachloride

Figure 2:
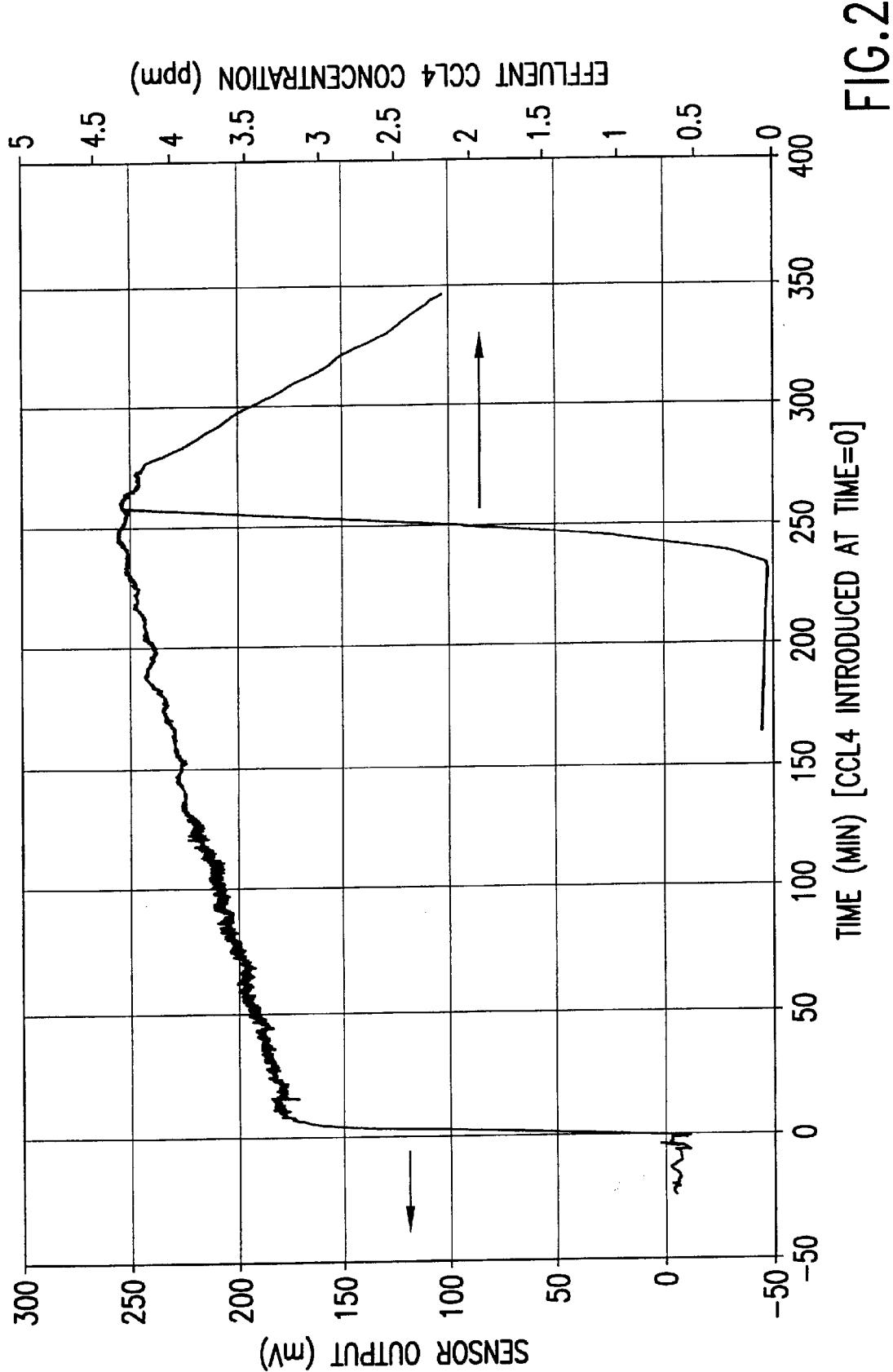
FIG. 2 shows the response of an ACC sensing element of the present invention with respect to changes in the concentration of carbon tetrachloride in air.

The detector of the present invention as is shown in FIG. 1 was used to demonstrate the detection of carbon tetrachloride in air. Each of the sensing elements was made of one layer of FM5/250 ACC (Calgon Carbon Corporation, Pittsburgh, Pa.). A stream of air having a flow rate of about 16 liter per minute (1/min.) and a relative humidity (RH) of about 20% was conducted overnight through the detector. The Wheatstone bridge was balanced and carbon tetrachloride was introduced into the stream of air to obtain a concentration of about 1000 ppm (by volume) $CCl_4$. The Wheatstone bridge immediately showed a large off-set voltage, as is shown in FIG. 2, indicating a measurable change in the electrical resistance of the first sensing element. The resistance of the first sensing element immediately decreased from 31.1 ohm to 27.8 ohm while that of the second sensing element decreased from 31.7 ohm to 29.7 ohm. If this stream of air had been a split stream from an air purification system which was designed to remove $CCl_4$, such a detection of the off-set voltage could be used to indicate a breakthrough of $CCl_4$ at the point of gas sampling. The flow was continued until the adsorbent in the pipe section was saturated with $CCl_4$ and $CCl_4$ was detected at the exit end of the detector, at which time the off-set voltage began to decrease as the difference between the resistances of the two sensing elements began to decrease.

EXAMPLE 2

Detection of Sulfur Dioxide

Figure 3:
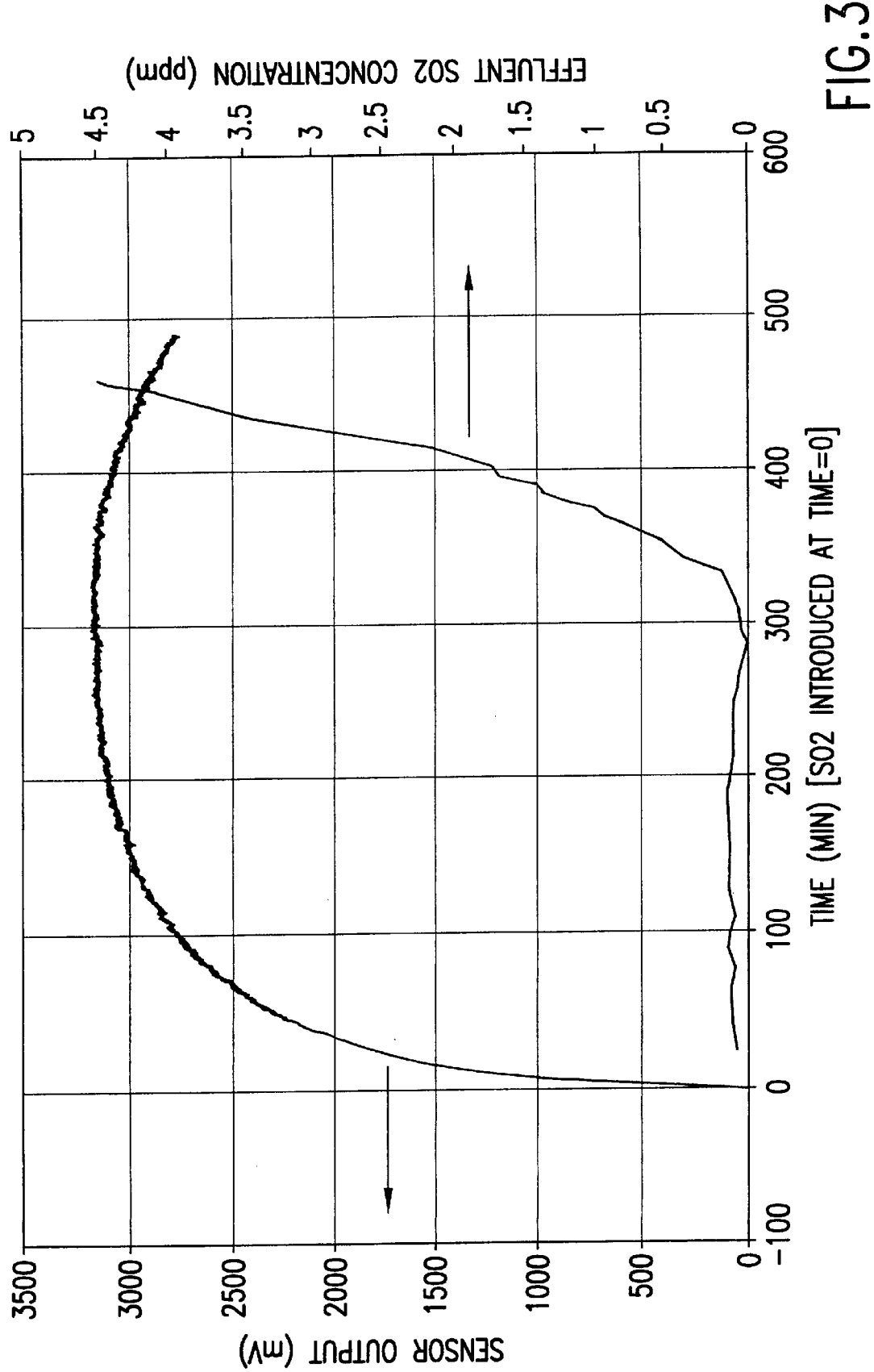
FIG. 3 shows the response of an ACC sensing element of the present invention with respect to changes in the concentration of $SO_2$ in air.

A detector having the same construction and dimension as that used in Example 1 was tested for the detection of $SO_2$ in a stream of air. Air at a flow rate of about 32 1/rain. and about 50% RH was conducted through the detector overnight through the detector. Then the Wheatstone bridge was balanced and $SO_2$ was introduced into the air stream to obtain a concentration of about 550 ppm by volume. The Wheatstone bridge immediately showed a large positive off-set voltage, as is shown in FIG. 3, indicating a large change in the electrical resistance of the first sensing element. The resistance of the first sensing element immediately decreased from 25.7 ohm to 6.9 ohm while that of the second (reference) element decreased from 13.3 ohm to 10.7 ohm. If this stream of air had been a split stream from an air purification system which wag designed to remove $SO_2$, such a detection of the off-set voltage could be used to indicate a breakthrough of $SO_2$ at the point of gas sampling. The flow was continued until the adsorbent portion in the pipe section was saturated with $SO_2$ and $SO_2$ was detected at the exit end of the detector, at which time the off-set voltage of the Wheatstone bridge began to decrease as the resistance of the reference sensing element began to decrease more rapidly.

EXAMPLE 3

Detection of Ammonia

Figure 4:
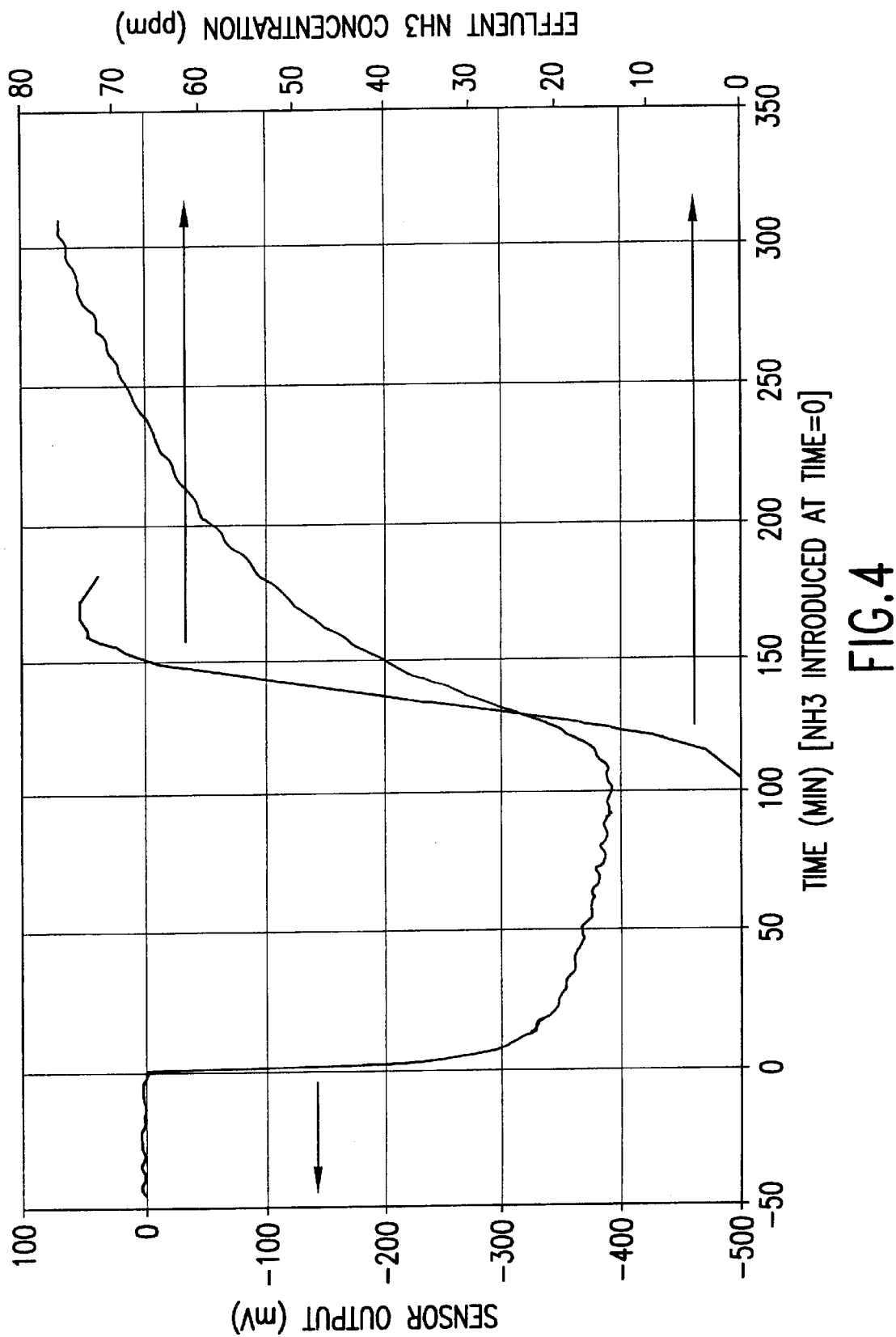
FIG. 4 shows the response of an ACC sensing element of the present invention with respect to changes in the concentration of ammonia in air.

A detector having the same construction and dimension as that used in Example 1 was tested for the detection of ammonia in a stream of air. The sensing elements in this example were made of FM5/250 ACC impregnated with about 15 percent (by weight) citric acid. The pipe section contained about 100 g of a granular carbon impregnated with 15 percent (by weight) citric acid. Air at a flow rate of about 32 1/min. and about 50% RH was conducted through the detector overnight. Then the Wheatstone bridge was balanced and ammonia was introduced into the air stream to obtain a concentration of about 500 ppm by volume. The Wheatstone bridge immediately showed a large negative off-set voltage, as is shown in FIG. 4, indicating a large change in the electrical resistance of the first sensing element. The resistance of the first sensing element immediately increased from 18.4 ohm to 24.8 ohm while that of the second (reference) element increased from 20.0 ohm to 25.9 ohm. If this stream of air had been a split stream from an air purification system which was designed to remove ammonia, such a detection of the off-set voltage could be used to indicate a breakthrough of ammonia at the point of gas sampling. The flow was continued until the adsorbent portion in the pipe section was saturated with ammonia and ammonia was detected at the exit end of the detector, at which time the off-set voltage of the Wheatstone bridge began to increase as the resistance of the reference sensing element began to increase more rapidly.

EXAMPLE 4

Detection of Sucrose in an Aqueous Solution

Figure 5:
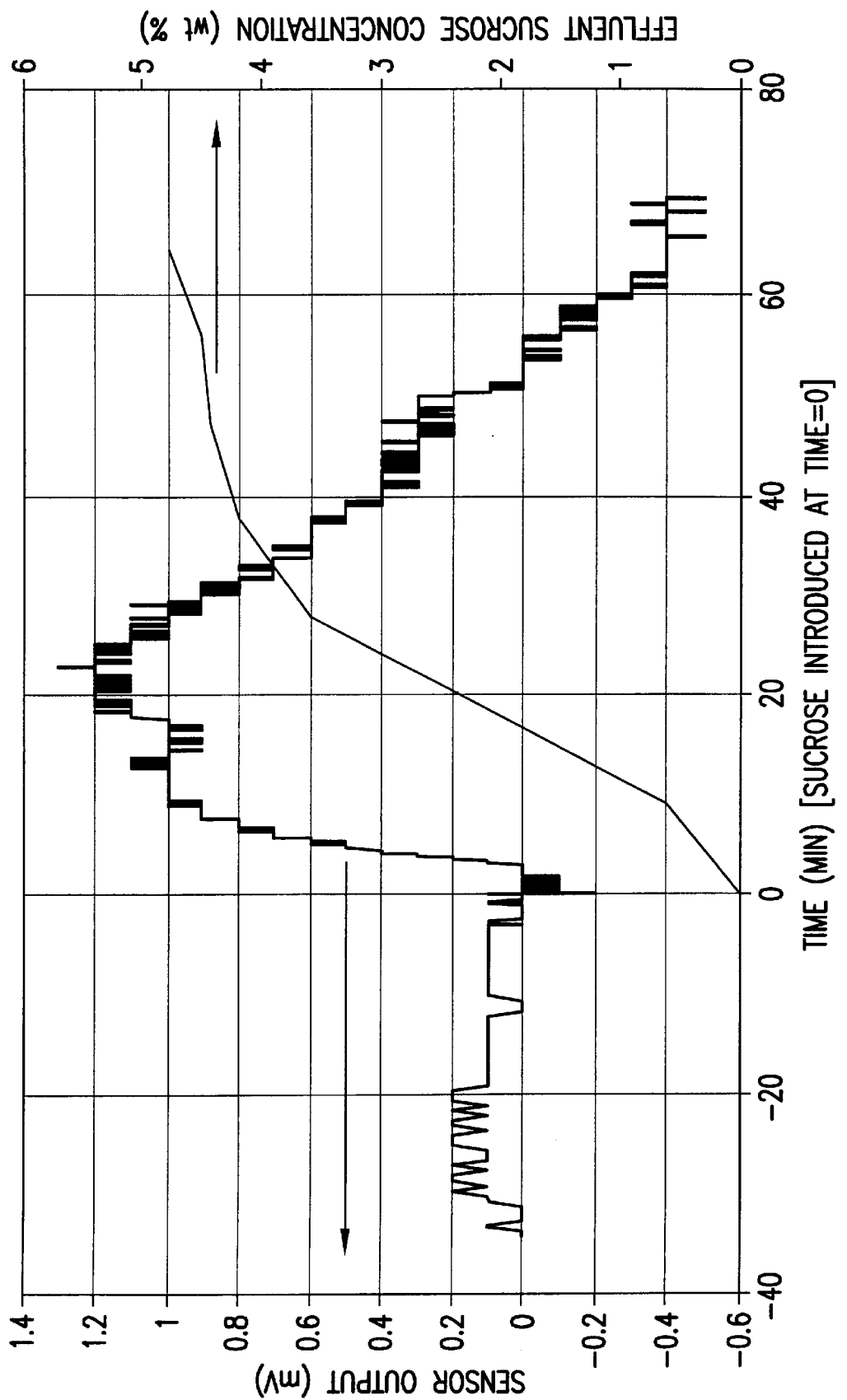
FIG. 5 shows the response of an ACC sensing element of the present invention with respect to changes in the concentration of sucrose in water.

A detector having the same construction and dimension as that used in Example 1 was tested for the detection of sucrose in a stream of water. The sensing elements in this example were FM5/250 ACC. The pipe section contained about 150 g of a granular carbon. Deionized water at a flow rate of about 90 cm$^3$/min. was conducted through the detector overnight. Then the Wheatstone bridge was balanced and a five-percent (by weight) sucrose aqueous solution was introduced into the detector. The Wheatstone bridge immediately showed a positive off-set voltage, as is shown in FIG. 5, indicating a change in the electrical resistance of the first sensing element. Data for the resistances of the sensing elements were not recorded. However, the increase in the off-set voltage indicated that the magnitude of the change in the resistance of the first sensing element is larger than that of the second or reference sensing element. If this stream of solution had been a split stream from a water purification system which was designed to remove sucrose, such a detection of the off-set voltage could be used to indicate a breakthrough of sucrose at the point of sampling. The flow was continued until the granular carbon adsorbent portion in the pipe section was substantially saturated with sucrose and sucrose was detected at the exit end of the detector, at which time the off-set voltage of the Wheatstone bridge began to decrease as the resistance of the reference sensing element began to approach that of the first sensing element.

EXAMPLE 5

Detection of Isopropyl Alcohol ("IPA") in an Aqueous Solution

Figure 6:
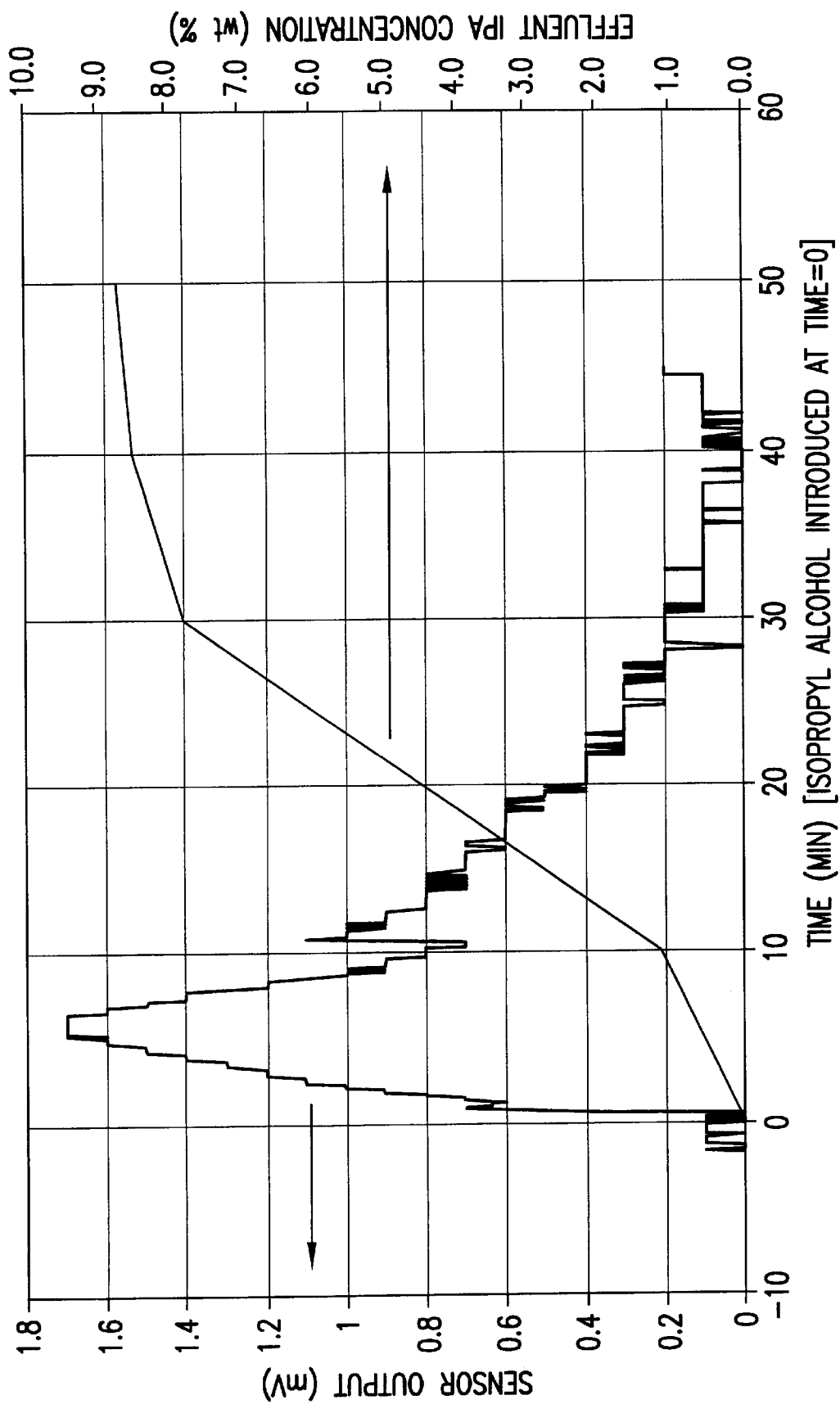
FIG. 6 shows the response of an ACC sensing element of the present invention with respect to changes in the concentration of isopropyl alcohol ("IPA") in water.

A detector having the same construction and dimension as that used in Example 1 was tested for the detection of IPA in a stream of water. The sensing elements in this example were FM5/250 ACC. The pipe section contained about 150 g of a granular carbon. Deionized water at a flow rate of about 90 cm$^3$/min. was conducted through the detector overnight. Then the Wheatstone bridge was balanced and a 9.1% (by volume) IPA aqueous solution was introduced into the detector. The Wheatstone bridge immediately showed a positive off-set voltage, as is shown in FIG. 6, indicating a change in the electrical resistance of the first sensing element. Data for the resistances of the sensing elements were not recorded. However, the increase in the off-set voltage indicated that the magnitude of the change in the resistance of the first sensing element is larger than that of the second or reference sensing element. If this stream of solution had been a split stream from a water purification system which was designed to remove IPA, such a detection of the off-set voltage could be used to indicate a breakthrough of IPA at the point of sampling. The flow was continued until the granular carbon adsorbent portion in the pipe section was substantially saturated with IPA and IPA was detected at the exit end of the detector, at which time the off-set voltage of the Wheatstone bridge began to decrease as the resistance of the reference sensing element began to approach that of the first sensing element.

EXAMPLE 6

Figure 7:
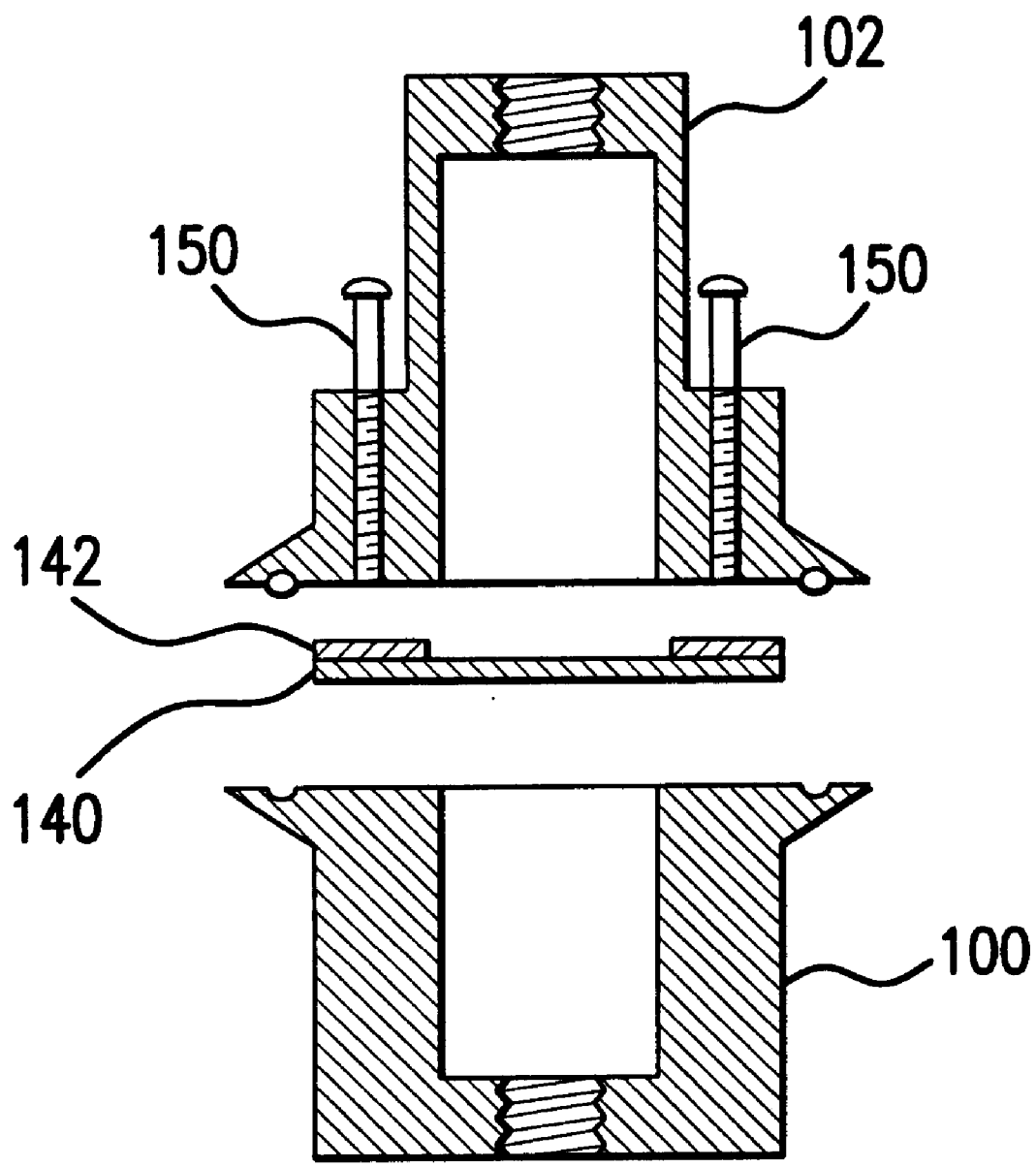
FIG. 7 shows a schematic diagram of the second embodiment of the present invention.

Detection of Butane Breakthrough from a Purification System using Granular Activated Carbon A granular activated carbon bed having a diameter of about 2 feet and a depth of about 15.5 inches was used to purified a stream of air contaminated with n-butane. The carbon bed was equipped with sample taps at 3, 9, and 15 inches from the inlet end. A second embodiment of the detector of the present invention was used to detect the adsorption front of n-butane as it progresses from the inlet to the outlet end of the carbon bed. FIG. 7 shows the cross-sectional view of a detector cell of the second embodiment of the present invention. Each sensing element is disposed in a separate cell housing which comprises matching halves 100 and 102 which are made of, for example, a polymeric material. The ACC sensing element 140 is disposed between the two cell housing halves and secured in place by bolts 150. The ACC sensing element is provided with a brass electrode 142 to enhance the electrical contact between the sensing element 140 and the bolts 150, which also serve to connect electrical leads to a resistance measuring device. A stream of fluid mixture, the change in the composition of which is desired to be detected, is conducted through the cell housing past the ACC sensing element. As a minor component of the fluid mixture adsorbs in the ACC material of the sensing element, its resistance changes and a detection is indicated. A Wheatstone bridge was used to detect a change in the resistance of the sensing element at the 9-inch tap relative to the reference sensing element.

Figure 8:
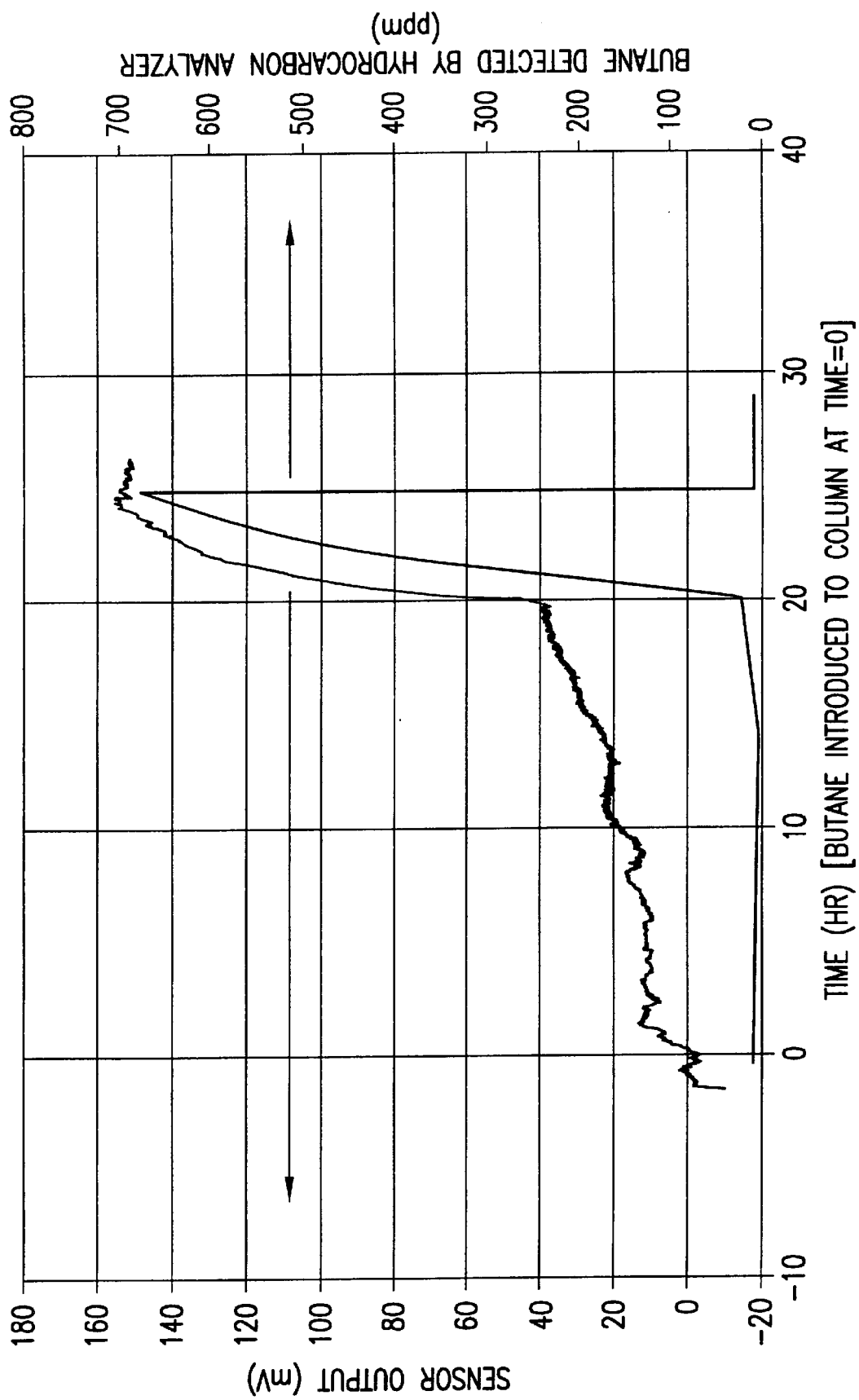
FIG. 8 shows the response of an ACC sensing element of the present invention with respect to changes in the concentration of n-butane in air.

One detector cell was provided at the 9-inch tap and another serving as the reference was provided at the outlet end of the granular carbon bed. Air at about 27% RH and about 27 ° C. containing about 950 ppm (by volume) n-butane was conducted through the carbon bed at about 100 ft$^3$/min. A split stream of 10 l/min. was drawn into each detector cell. Another split stream at the 9-inch tap was also directed to a hydrocarbon analyzer equipped with a flame ionization detector to measure the concentration of n-butane. FIG. 8 shows the Wheatstone bridge off-set voltage in relation to the n-butane concentration. When the n-butane concentration began to increase sharply at the 9-inch tap, the Wheatstone bridge off-set voltage also increased sharply, indicating a substantially simultaneous correspondence between the concentration change and the voltage change.

The foregoing examples show that the detector of the present invention is capable of indicating changes in concentrations of a wide variety of compounds in both gas and liquid mixtures. Thus, detectors of the present invention can be successfully employed to indicate breakthrough of components of fluid mixtures.

While the foregoing has described the preferred embodiments and modes of operation of the present invention, it should be appreciated that numerous variations, changes, and equivalents may be made to these embodiments and modes of operation without departing from the scope of the present invention as defined in the following claims.

What is claimed is:

1. An apparatus for detecting changes in concentrations of minor components of a fluid mixture comprising two sensing elements in a housing, through which the fluid mixture is conducted, said sensing elements comprising activated carbon cloth and exhibiting a measurable electrical resistance in response to any said concentration changes when said sensing elements are exposed to or in contact with said fluid mature, and a means for detecting said electrical resistance.

2. An apparatus for detecting changes in concentrations of minor components of a fluid mixture as recited in claim 1 further including an adsorbent disposed between said sensing elements.

3. An apparatus for detecting changes in concentrations of minor components of a fluid mixture as recited in claim 1 wherein said activated carbon cloth is capable of adsorbing at least one component of said fluid mixture.

4. An apparatus for detecting changes in concentrations of minor components of a fluid mixture as recited in claim 1 wherein said sensing elements have substantially equal electrical resistance before exposure to or contact with said fluid mixture.

5. A method for detecting changes in concentrations of minor components of a fluid mixture comprising the steps of:
   a. conducting a stream of the fluid mixture sequentially through thesensing elements of the apparatus of claim 1 or 2;
   b. measuring an electrical resistance of each of the sensing elements;
   c. recording a change in the electrical resistance of the first sensing element relative to the electrical resistance of the second sensing element; and
   d. associating the change in the electrical resistance of the first sensing element with the change in the concentrations of components of the fluid mixtures.

6. A method for detecting changes in concentrations of minor components of a fluid mixture comprising the steps of:
   a. conducting a stream of the fluid mixture sequentially through the sensing elements of the apparatus of claim 3,
   b. measuring an electrical resistance of each of the sensing elements;
   c. recording a change in the electrical resistance of the first sensing element relative to the electrical resistance of the second sensing element; and
   d. associating the change in the electrical resistance of the first sensing element with the change in the concentrations of components of the fluid mixture.

7. A method for detecting changes in concentrations of minor components of a fluid mixture comprising the steps of:
   conducting a stream of the fluid mixture sequentially though thesensing elements of the apparatus of claim 4,
   b. measuring an electrical resistance of each of the sensing elements;
   c. recording a change in the electrical resistance of the first sensing element relative to the electrical resistance of the second sensing element; and
   d. associating the change in the electrical resistance of the first sensing element with the change in the concentrations of components of the fluid mixture.

8. An apparatus for detecting changes in concentrations of minor components of a fluid mixture as recited in claim 1, wherein said housing comprises a first chamber and a second chamber, one of said sensing elements being disposed in said first chamber and the other of said sensing elements being disposed in said second chamber.

9. An apparatus for detecting changes in concentrations of minor components of a fluid mixture as recited in claim 8, further including an adsorbent disposed between said sensing elements.

10. An apparatus for detecting changes in concentrations of minor components of a fluid mixture as rented in claim 1 or 8 wherein said cloth comprises of a woven or nonwoven fiber selected from the group consisting of natural fiber, man-made fiber, synthetic fiber and a combination thereof.

11. An apparatus for detecting changes in concentrations of minor components of a fluid mixture as recited in claim 1 or 8 wherein said cloth comprises an electrically conducting sheet having activated carbon particles therein.

* * * * *

UNITED STATES PATENT AND TRADEMARK OFFICE
CERTIFICATE OF CORRECTION

PATENT NO.      : 6,422,059 B1
DATED           : July 23, 2002
INVENTOR(S)     : Greenbank et al.

It is certified that error appears in the above-identified patent and that said Letters Patent is hereby corrected as shown below:

<u>Column 8,</u>
Line 60, please delete "mature" and insert therefor -- mixture --

<u>Column 9,</u>
Line 12, please insert a space between the word "the" and before the word "sensing"
Line 22, please delete "mixtures" and insert therefor -- mixture --

<u>Column 10,</u>
Line 6, please insert a space between the word "the" and before the word "sensing"
Line 27, please delete "rented" and insert therefor -- recited --

Signed and Sealed this

Twenty-ninth Day of July, 2003

JAMES E. ROGAN
*Director of the United States Patent and Trademark Office*